United States Patent
Volgyesi

[11] Patent Number: 6,019,732
[45] Date of Patent: Feb. 1, 2000

[54] DEVICE AND METHOD FOR MEASURING TIDAL VOLUME

[76] Inventor: George A. Volgyesi, 36 Gatehead Road, Willowdale Ontario, Canada, M2J 2P5

[21] Appl. No.: 09/057,524

[22] Filed: Apr. 9, 1998

Related U.S. Application Data

[60] Provisional application No. 60/043,286, Apr. 11, 1997.

[51] Int. Cl.[7] .................................................. A61B 5/02
[52] U.S. Cl. ........................... 600/534; 600/529; 600/535
[58] Field of Search ............................... 600/529, 534–5, 600/587

[56] References Cited

U.S. PATENT DOCUMENTS

| | | | |
|---|---|---|---|
| 4,576,179 | 3/1986 | Manus et al. | 600/534 |
| 4,817,625 | 4/1989 | Miles | 600/534 |
| 4,895,160 | 1/1990 | Reents | 600/535 |
| 5,086,785 | 2/1992 | Gentile et al. . | |
| 5,131,399 | 7/1992 | Sciarra | 600/534 |
| 5,161,541 | 11/1992 | Bowman et al. . | |
| 5,271,412 | 12/1993 | Shtalryd et al. . | |
| 5,273,036 | 12/1993 | Kronberg et al. . | |
| 5,316,009 | 5/1994 | Yamada . | |
| 5,331,968 | 7/1994 | Williams et al. | 600/534 |
| 5,467,768 | 11/1995 | Suda et al. | 600/534 |
| 5,513,648 | 5/1996 | Jackson . | |
| 5,832,592 | 11/1998 | Bowman et al. . | |

*Primary Examiner*—Robert L. Nasser
*Attorney, Agent, or Firm*—Bereskin & Parr

[57] ABSTRACT

A device for monitoring tidal volume in a subject comprising a flexible substrate for attachment to an animal or human whose tidal volume is to be monitored; sensing means attached to the substrate and connectable into an electric circuit which converts changes in tidal volume in the animal or human to a signal output, the sensing means comprising a series of semiconductive sensors and conductive sensors. A method for monitoring tidal volume in a subject using the device is also described.

20 Claims, 12 Drawing Sheets

DEVICE AND METHOD FOR MEASURING TIDAL VOLUME

This application claims benefit from U.S. Provisional Application No. 60/043,286 filed Apr. 11, 1997.

FIELD OF THE INVENTION

The invention relates to a device for monitoring tidal volume in a subject, and a method for monitoring tidal volume in a subject using the device.

BACKGROUND OF THE INVENTION

Various devices have been designed for monitoring tidal volumes in animals and humans during sleep and anesthesia. These devices include the pneumotachograph, impedance pneumograph, mercury in rubber transducer, and body plethysmograph.

Yamada (U.S. Pat. No. 5,316,009) describes an apparatus with a pressure sensor for detecting pressure in an air passage connecting a lung ventilator and the airway system of a patient, and a flow rate sensor for detecting flow rate in the air passage. Shtalry (U.S. Pat. No. 5,271,412) describes a movement detector useful as an apnea monitor which includes a piezoelectric crystal transducer, a supporting member on one side of the transducer, and a collector member on the opposite side of the transducer. Kronberg (U.S. Pat. No. 5,273,036) describes a partial body plethysmograph to enable accurate modeling of a human's respiratory system for input frequencies of up to about 96 Hz using transfer impedance measurements. Jackson (U.S. Pat. No. 5,513,648) describes a method of measuring lung function in a subject including connecting a pneumotach in series with the subject's airway and taking pressure readings upstream and downstream of a fixed resistance element in the pneumotach.

The prior art devices present one or more disadvantages including inconvenience of use and costly production of the devices. Therefore, there is a need for a simple and reliable means for monitoring tidal volumes.

Gentile et al. (U.S. Pat. No. 5,086,785) describe a sensor for primarily detecting angular displacement of fingers of the hand, movement of arms and legs and joints. The angular displacement sensors may be disposed on a glove worn by a user such that the movements of the fingers of the user can be supplied as inputs to a computer to control robotics, video games, the movement of graphics, or other displayed materials on a display terminal. The sensor has a substrate and sensing means attached to the substrate and connectable to an electric circuit. Several embodiments are disclosed including a conductive elastomer sensor, a conductive ink sensor, a sliding resistor sensor, a force sensitive sensor, and a conductive fluid sensor.

SUMMARY OF THE INVENTION

The present inventor has developed a device for monitoring tidal volume in a subject. The device comprises a flexible substrate for attachment to a subject whose tidal volume is to be monitored, and sensing means attached to the substrate and connectable into an electric circuit which converts changes in tidal volume in the subject to a signal output, the sensing means comprising a series of semiconductive sensors and conductive sensors. The sensing means are preferably selected to provide a linear relationship between signal output and tidal volume. The signal output of the device has been found to correlate to the step increase in positive end expiratory pressure (PEEP). The device can also be used simultaneously or separately as a cardiac monitor to monitor heart rate.

The device has the following advantages: (1) it is useful without any other devices for monitoring tidal volume; (2) it is convenient to use and inexpensive to produce; (3) there is no electrical contact with the subject; (4) there is a high signal to noise ratio; (5) its application is fast and easy; (6) it does not impede the mobility of the subject; (7) existing monitors can be easily modified to incorporate the device; and (8) it is portable and has low power requirements.

The invention also relates to a method for monitoring tidal volume in a subject comprising (a) attaching a device to the subject wherein the device comprises a substrate for attachment to the chest or abdomen of the subject, and sensing means attached to the substrate and connectable into an electric circuit which converts changes in tidal volume in the subject to a signal output, the sensing means comprising a series of semiconductive sensors and conductive sensors; (b) detecting signal output from the device; and (c) monitoring the tidal volume by determining the frequency and intensity of the signal output. The sensing means are preferably selected to provide a linear relationship between signal output and tidal volume.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

As hereinbefore mentioned, the present invention provides a device for monitoring tidal volume in a subject such as an animal or human subject. Tidal volume refers to the changes to the subject caused by the expansion and contraction of the lungs, and includes the frequency of breathing.

The device consists of a substrate for attachment to a subject whose tidal volume is to be monitored. The substrate may be flexible and it may or may not be elastic. The substrate may be composed of plastic, plastic film, fabric, paper, natural or synthetic rubber or other elastomeric materials, and other materials that sensing means can be attached to. An example of a suitable flexible substrate is a Mylar™ film or Captan. The substrate may be in a variety of shapes including a disc-, donut, cuboid, or U-shaped configuration.

The substrate has sensing means attached to it which are connectable into an electric circuit. The sensing means comprise a series of semiconductive sensors and conductive sensors. The sensing means are preferably attached to both sides of the substrate.

In an embodiment of the invention the semiconductive sensors comprise semiconductive ink or paint deposited on the substrate. The semiconductive ink may be prepared from a durable stretchable ink formula, and a brittle ink formula. Suitable inks which contain both ink types are those used for making potentiometers such as those available from Amtech International, Lot 922349. In order to obtain a higher signal to noise ratio, it is preferable to use a higher amount of the brittle ink formula.

The conductive sensors comprise conductive material that is selectively deposited over the semiconductive ink to provide the resistance range needed for measuring tidal volumes. The conductive material is deposited so that it creates a series of alternate conductive and semiconductive regions. Suitable conductive materials include metallic materials such as copper. The semiconductive and conductive materials are deposited on the substrate using conventional techniques such as printing.

In an embodiment of the invention, the device has a U-shaped configuration, and when the device is prepared the substrate and sensing means are prestretched in the same orientation. For example, the substrate may be flexed prior to printing the sensing means on the concave side of the substrate.

In another embodiment of the invention, the device has a disc-shaped or donut-shaped substrate, and the sensing means are deposited in circular or zigzag patterns on the substrate.

The device or part of the device may be coated with a substance that facilitates the attachment of the device to the subject to be monitored. For example, the device or part of the device may be coated with foam to form a pad, and the pad may be coated with an adhesive substance. The device may also be shielded to be less sensitive to interference from electrical sources, and accordingly suitable conductive materials (e.g. copper) may be deposited over the semiconductive regions and semiconductive/conductive regions. Further, the device may be coated with material to prevent changes in resistance caused by humidity. For example, the surface of the device may be covered with waterproof material such as waterproof tape.

Figure 1:
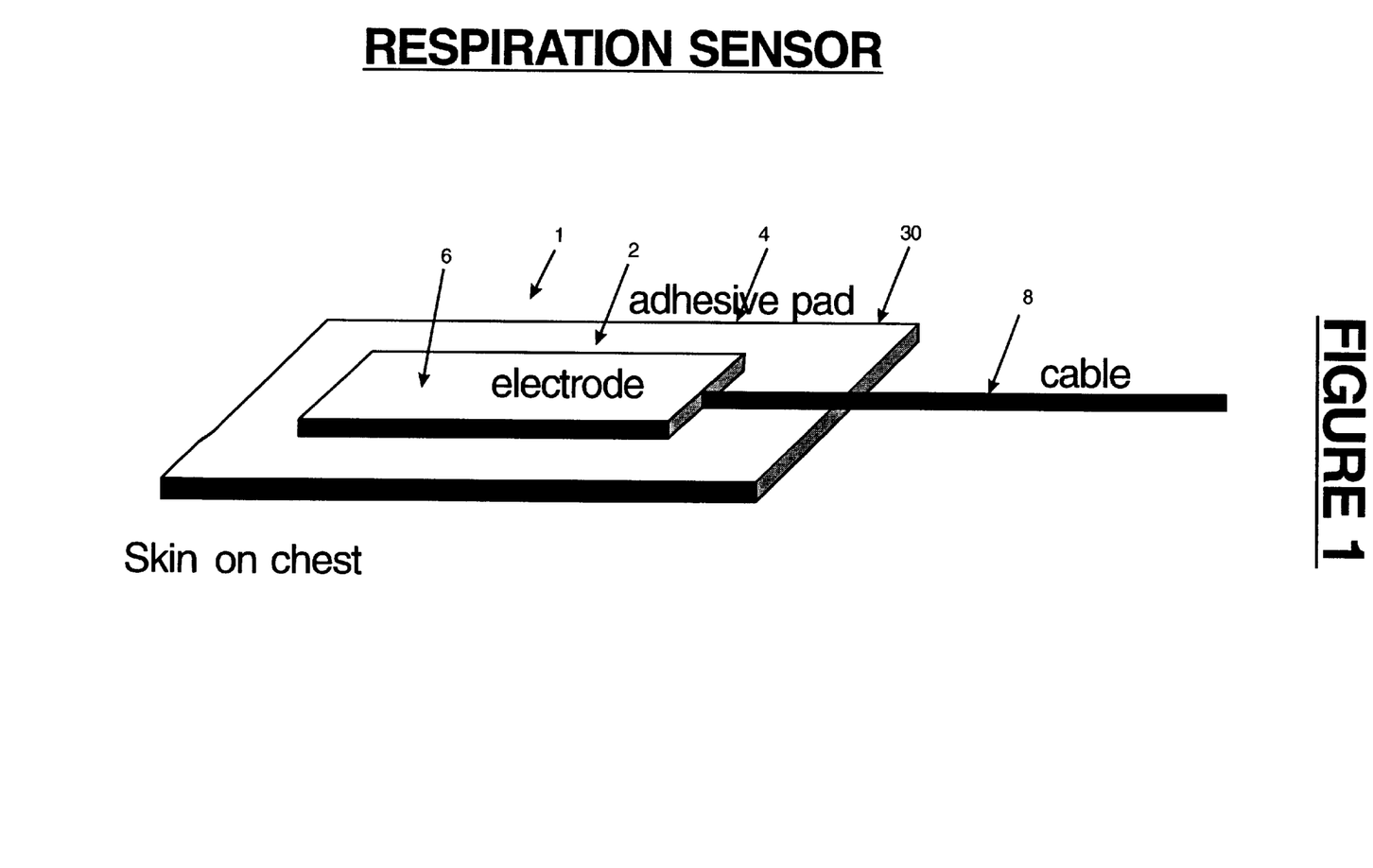
FIG. 1 is a perspective view of a device according to the present invention.

FIG. 1 shows a perspective view of a device 1 according to the invention. The device has a substrate 2 that has an adhesive surface 4 for attachment to the subject, e.g. the skin on the chest of a human subject. Sensing means 6 is attached to the surface of the substrate 2, and a cable 8 connects the device to an electric circuit. The device is coated with an adhesive pad 30.

Figure 2:
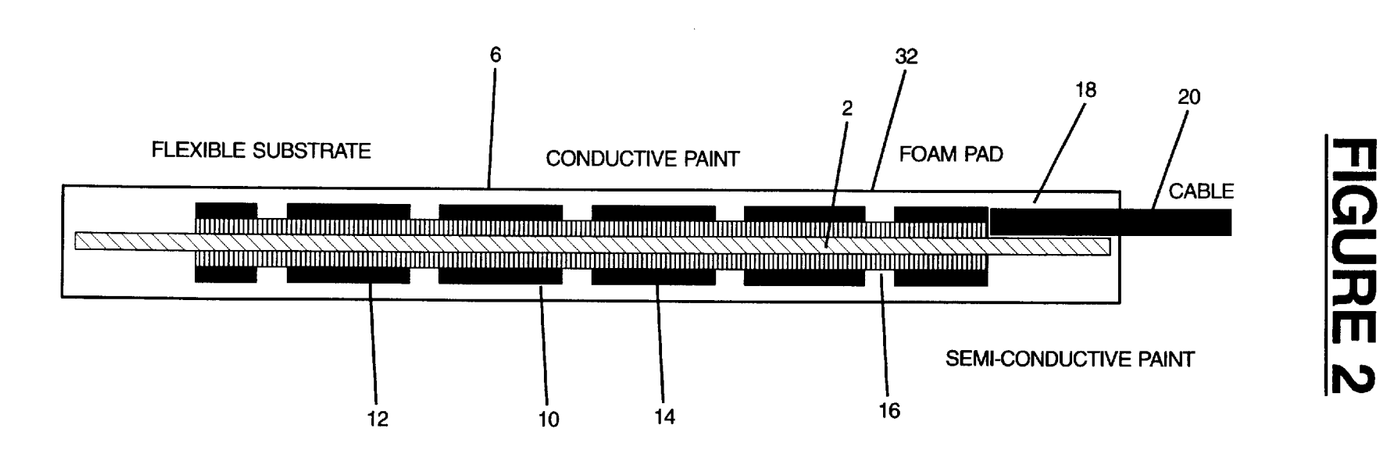
FIG. 2 is a top view of a device according to the invention.

FIG. 2 shows the sensing means 6 of the device according to the invention which includes a semiconductive paint 10 deposited along the length of a flexible substrate 2, and conductive paint 12 deposited on the semiconductive paint 10 creating a series of semiconductive/conductive 14 and semiconductive 16 regions. A foam pad 18 is deposited on the sensing means to facilitate attachment to the subject to be monitored. The sensing means 6 are connected to an electrical circuit by means of cable 20. The device is coated with a foam pad 32.

Figure 3:
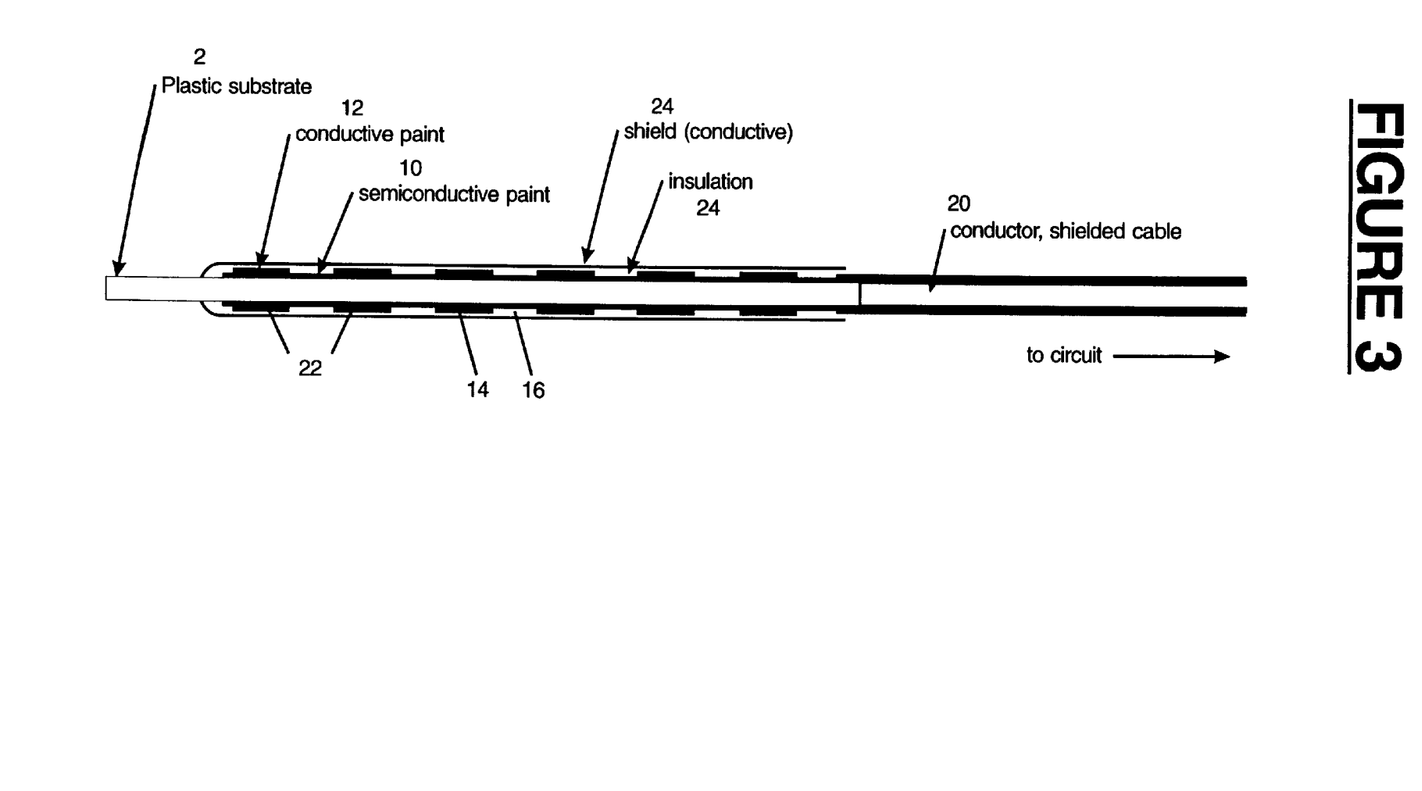
FIG. 3 is a cross-sectional view of a device according to the invention.

FIG. 3 shows an alternative embodiment of a device of the invention. The device includes semiconductive paint 10 deposited on both sides of a flexible substrate 2. The device has conductive paint 12 deposited in selected areas 22 over the semiconductive paint 10 creating a series of alternate semiconductive 16 and semiconductive/conductive regions 14. Insulation 24 is coated on the semiconductive regions 16. The device may be shielded to reduce interference from electrical sources and accordingly suitable conductive materials 24 may be deposited over the semiconductive regions 16 and semiconductive/conductive regions 14. Suitable conductive materials that may be used to shield the device include copper. A cable 20, preferably a conductor shielded cable, connects the device to an electric circuit.

Figure 9:
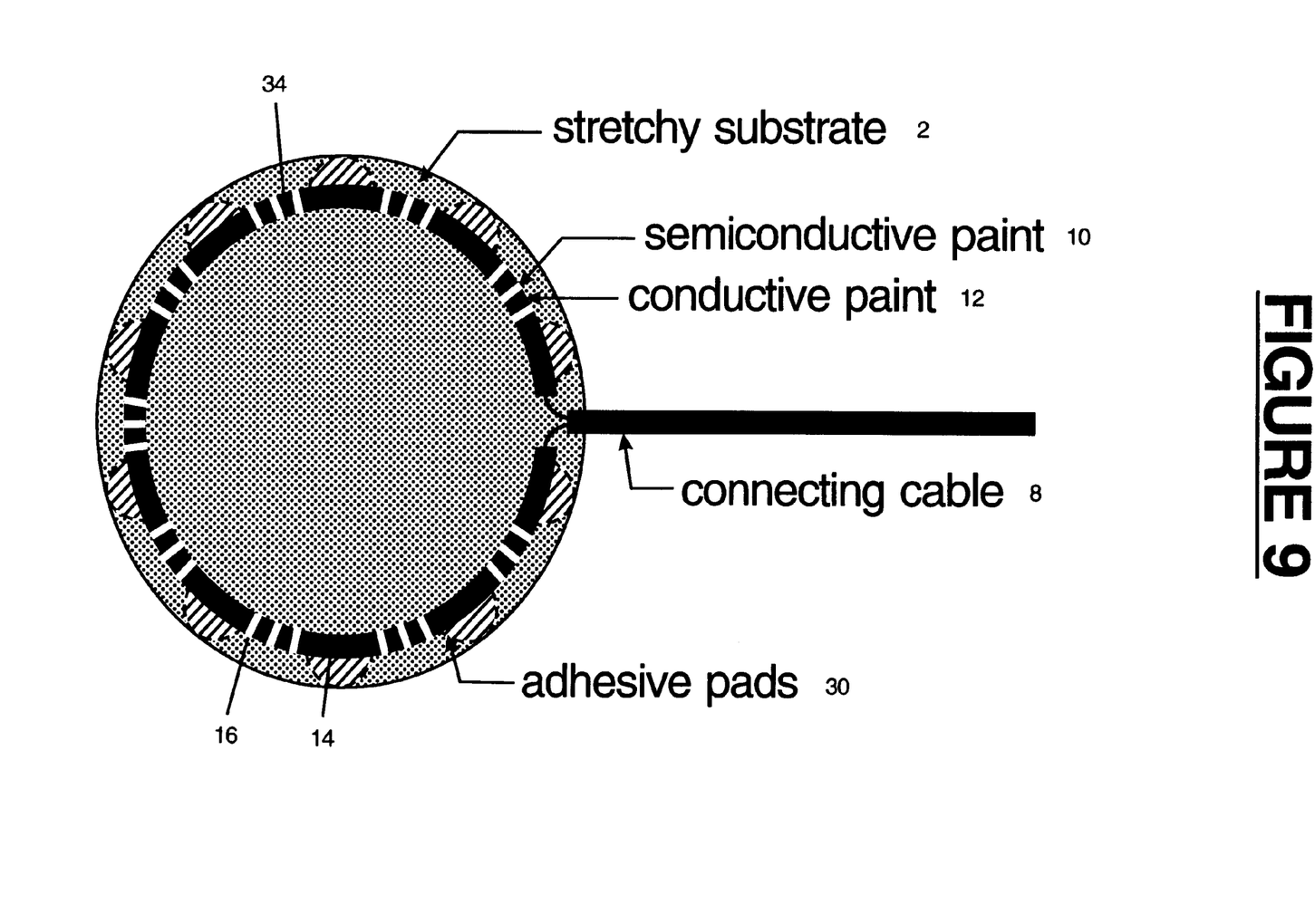
FIG. 9 is a top view of a disk-shaped device according to the invention.
Figure 10:
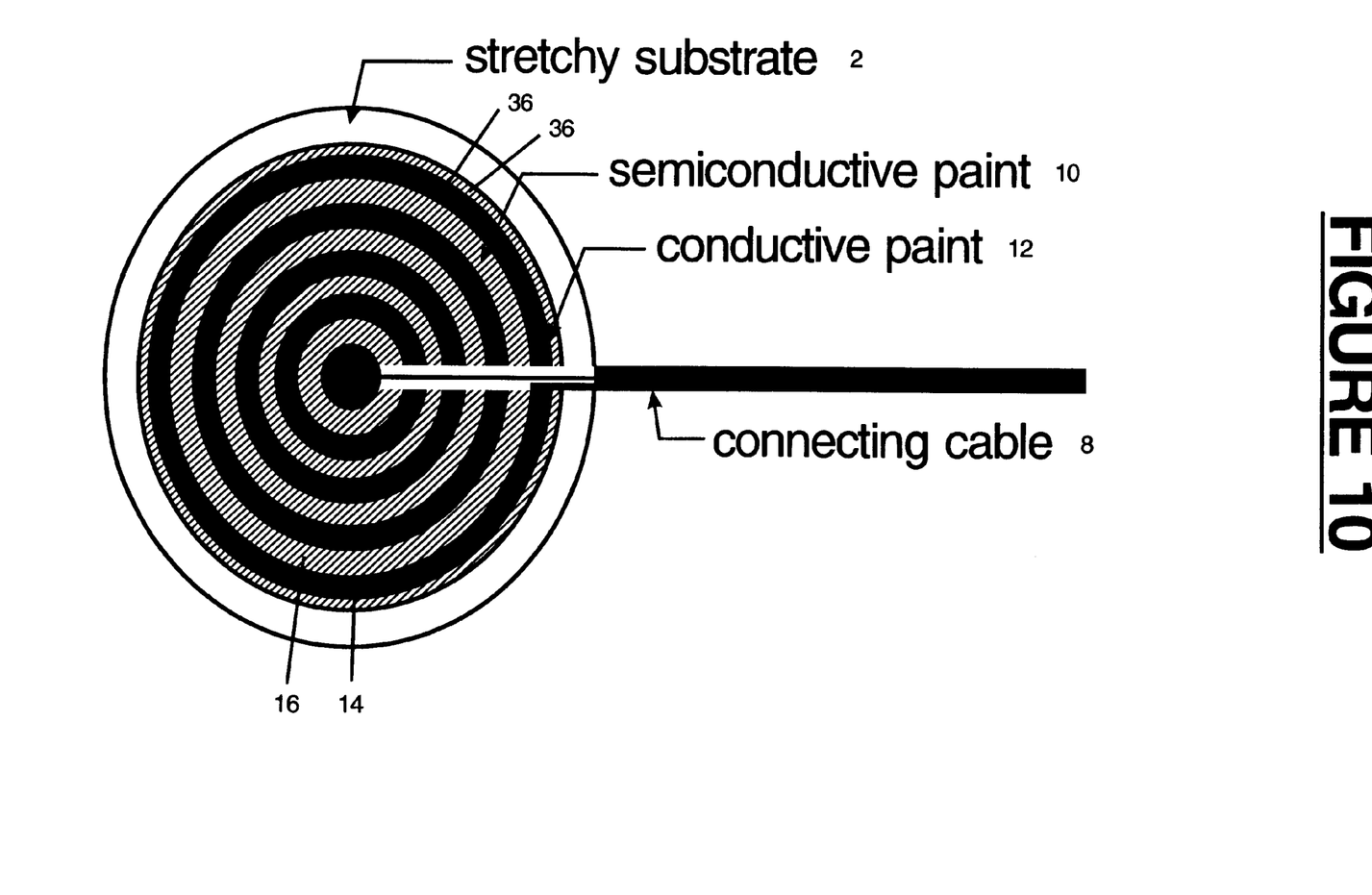
FIG. 10 is a top view of a disk-shaped device according to the invention.
Figure 11:
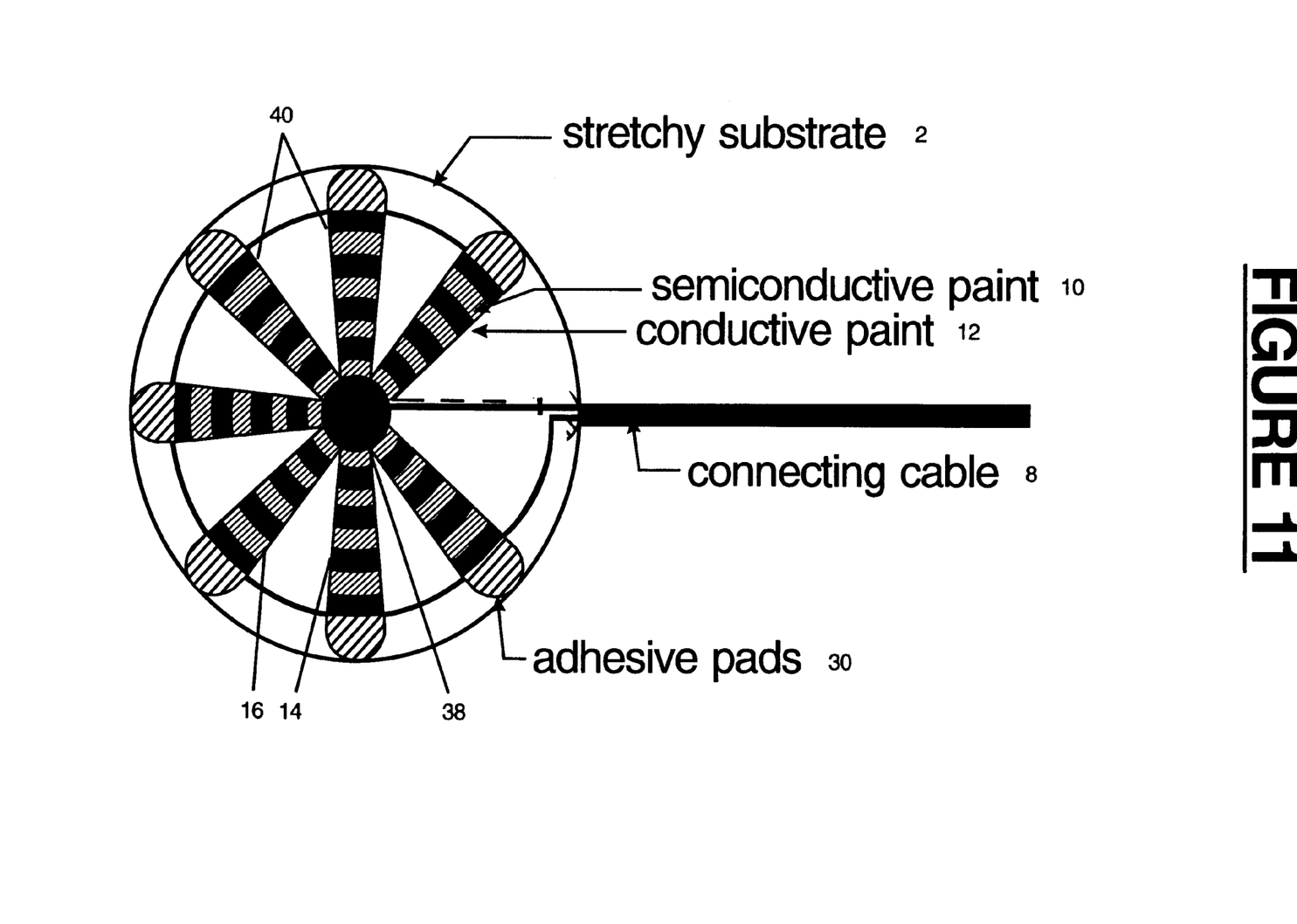
FIG. 11 is a top view of a disk-shaped device according to the invention.

FIGS. 9 to 11 show embodiments of a device of the invention that are discshaped. The device 1 in FIG. 9 has semiconductive paint 10 deposited as a ring on both sides of the flexible, preferably elastic, disc-shaped substrate 2, and conductive paint 12 deposited in selected areas over the semiconductive paint to form a ring 34 of alternate semiconductive/conductive regions. In FIG. 10, the device has semiconductive paint 10 deposited as a circle on both sides of the flexible, preferably elastic, disc-shaped substrate 2, and conductive paint 12 deposited as rings over the semiconductive paint to form semiconductive/conductive 14 and semiconductive 16 regions as alternate rings 36 on the substrate. The device 1 in FIG. 11 has semiconductive paint 10 deposited as an array of bands radiating from a central zone 38 (i.e. a spoke-pattern) on both sides of the flexible, preferably elastic, disc-shaped substrate 2, and conductive paint 12 deposited on selected areas over the semiconductive paint to form an array of bands 40 having alternate semiconductive/conductive 14 and semiconductive 16 regions.

Figure 12:
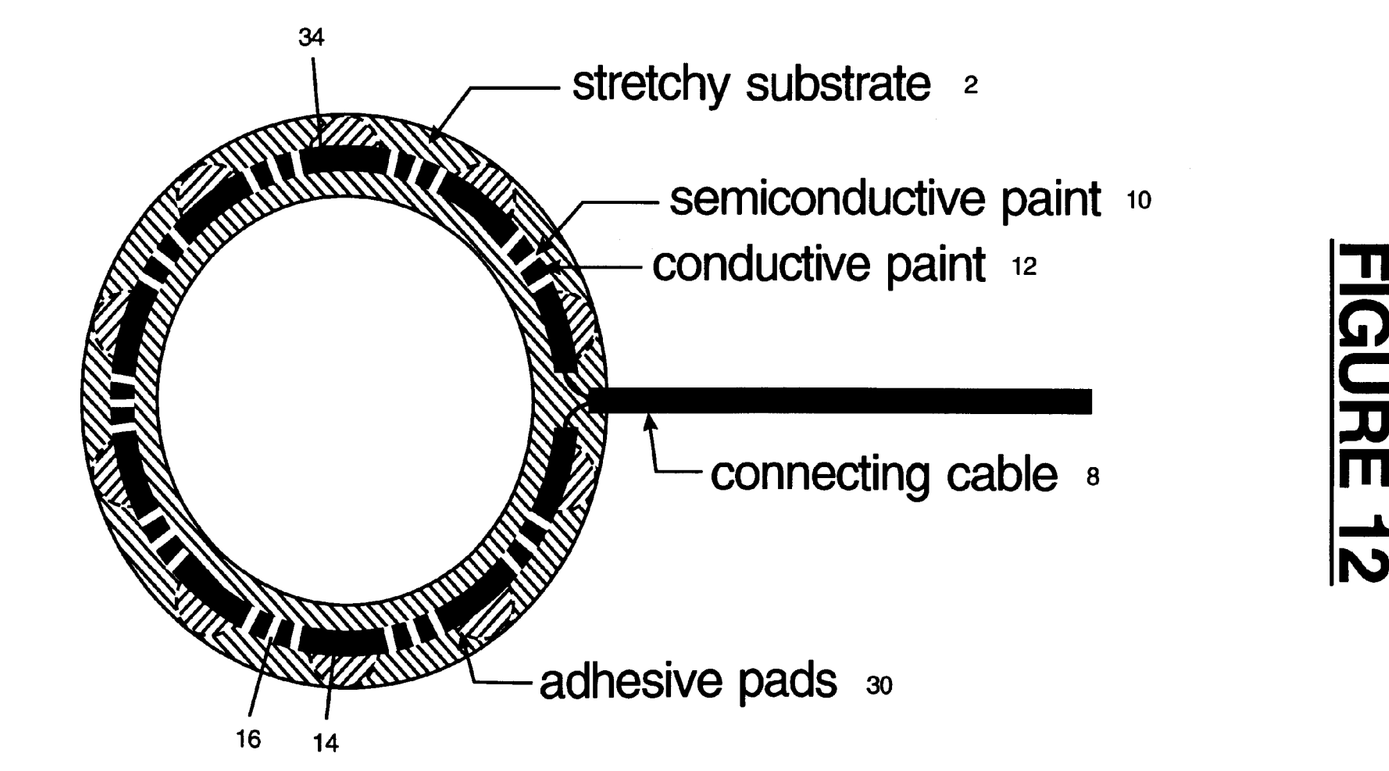
FIG. 12 is a top view of a donut-shaped device according to the invention.

FIG. 12 shows an embodiment of a device of the invention that is donut-shaped. The device in FIG. 12 has semiconductive paint 10 deposited as a ring on both sides of the flexible, preferably elastic, donut-shaped substrate 2, and conductive paint 12 deposited on selected areas over the semiconductive paint 10 to form a ring 34 of alternate semiconductive/conductive 14 and semiconductive 16 regions.

The substrates 2 of the devices 1 shown in FIGS. 9, 11, and 12 are also coated with adhesive pads 30, and the devices 1 shown in FIGS. 9 to 12 are connected via cable 8 to an electric circuit.

Figure 4:
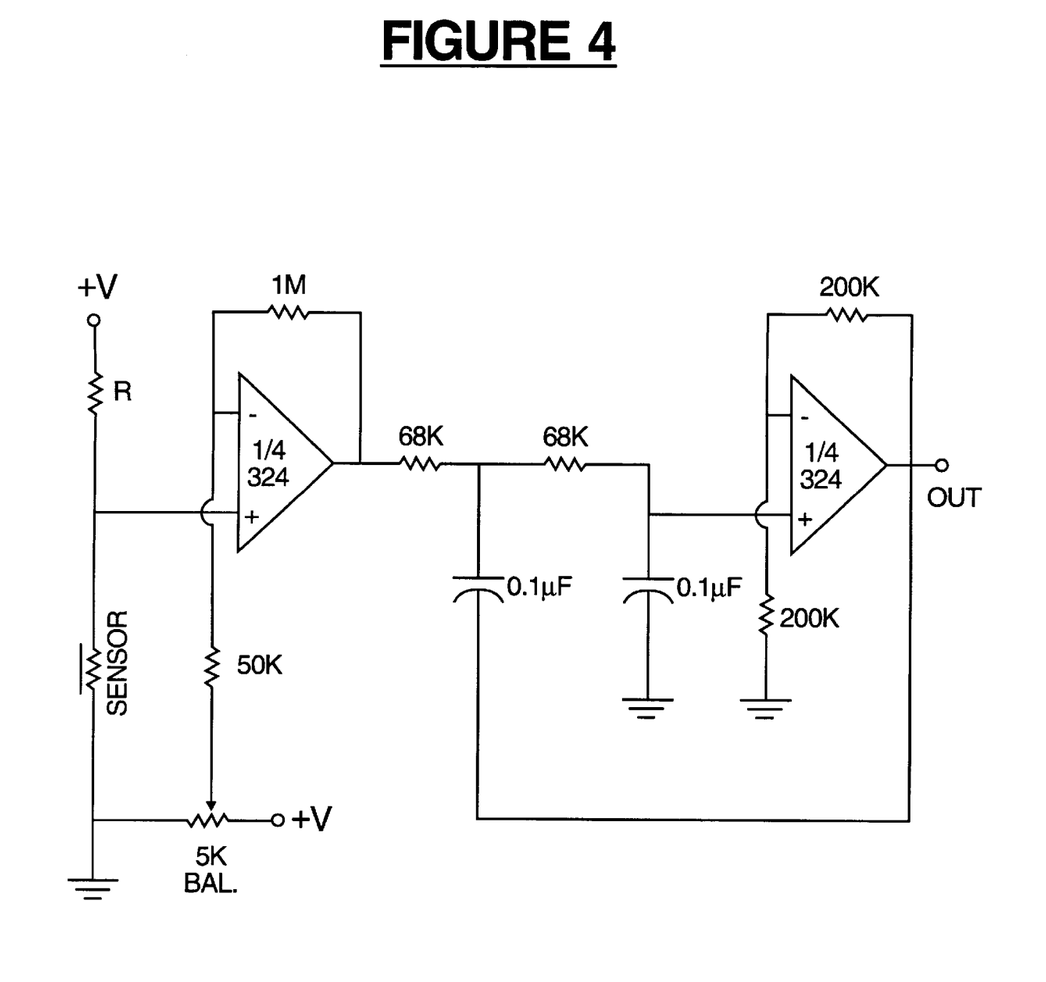
FIG. 4 shows an example of a circuit diagram for providing a signal from the device of the invention.

In use, one end of the device 1 according to the present invention is rested on the chest of an animal or human subject to be monitored. In response to changes in the expansion and contraction of the lungs in the subject the device reversibly changes its resistance. An electronic circuit converts the resistance changes to a signal voltage, which can be observed, measured, and recorded. FIG. 4 shows an example of a circuit diagram for providing a signal from the device. The magnitude of the signal voltage is a nearly linear function of tidal volume within a certain range.

The device according to the invention has many practical applications. It can be used for sleep studies, critical care situations, intra-operative monitoring, post-operative monitoring, apnea monitoring, magnetic resonance imaging, homecare, exercise monitoring, animal research, veterinary practice and space travel. The device may be particularly useful for studying lung function in animals and to identify potential therapeutics which may affect lung function.

The invention includes the device in combination with a ventilator. Devices composed of elastic material, (e.g. devices similar to those illustrated in FIGS. 9 to 12), may be particularly useful for inspiratory triggering of a ventilator in pressure support mode. When the device is fixed over the chest or abdomen of the subject, an inspiratory effort stretches the device in all directions, causing a change in resistance, which can trigger the ventilator. A motion artifact not associated with breathing effort would produce a much smaller signal which should not trigger the ventilator.

The device of the present invention may also be used simultaneously or separately as a cardiac monitor to monitor heart rate.

The following non-limiting example is illustrative of the present invention:

EXAMPLE

Figure 5:
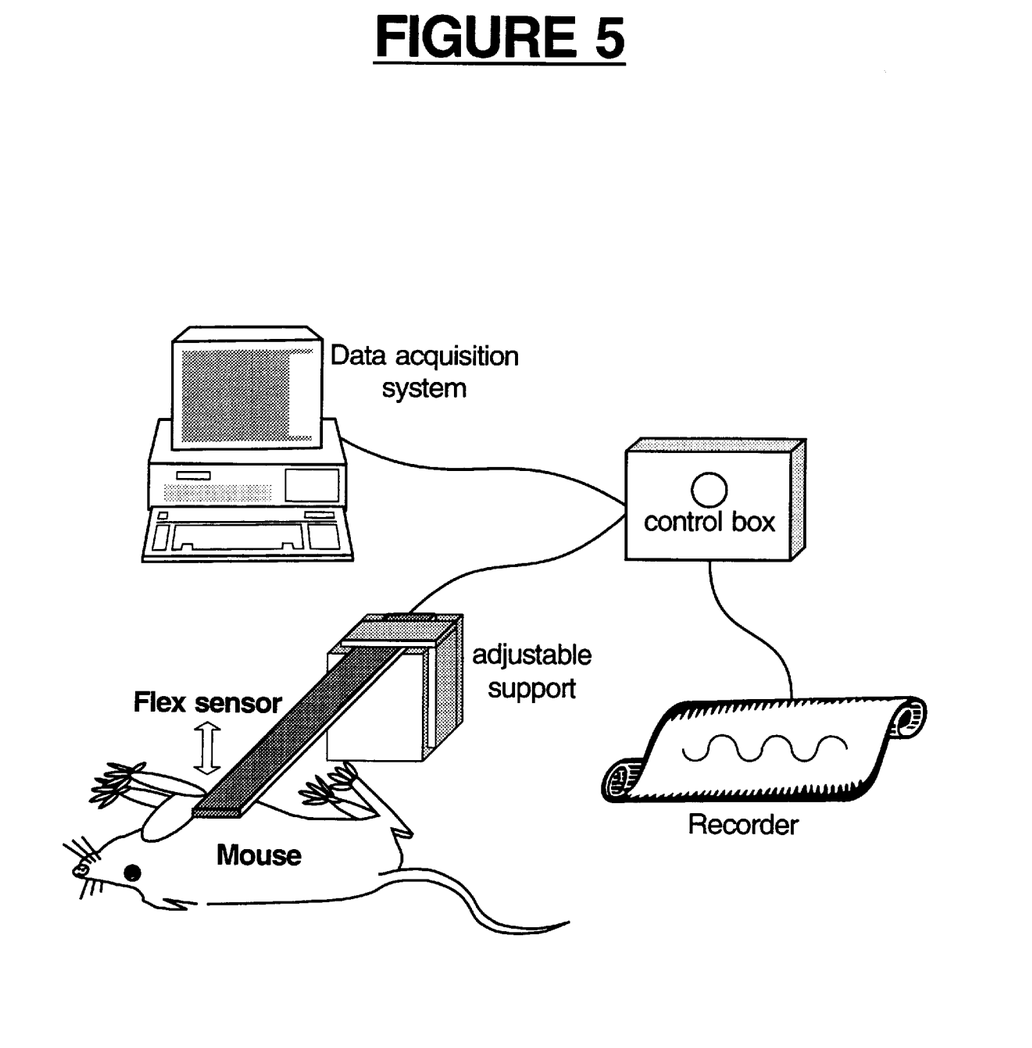
FIG. 5 is a schematic diagram showing the device in use in an animal model system.
Figure 6:
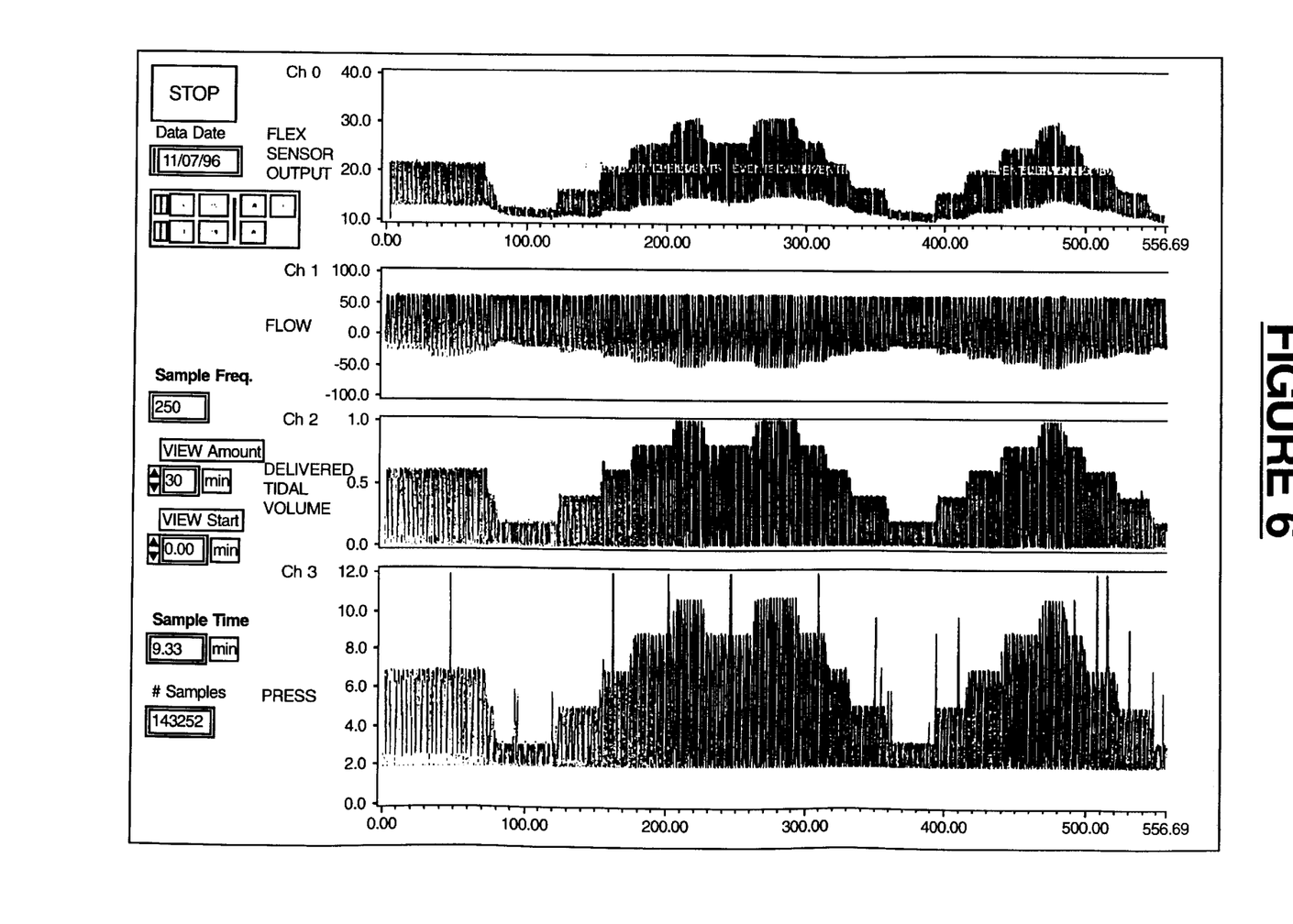
FIG. 6 is a graph showing the response of mice ventilated with a volume cycled ventilator to a device according to the invention.
Figure 7:
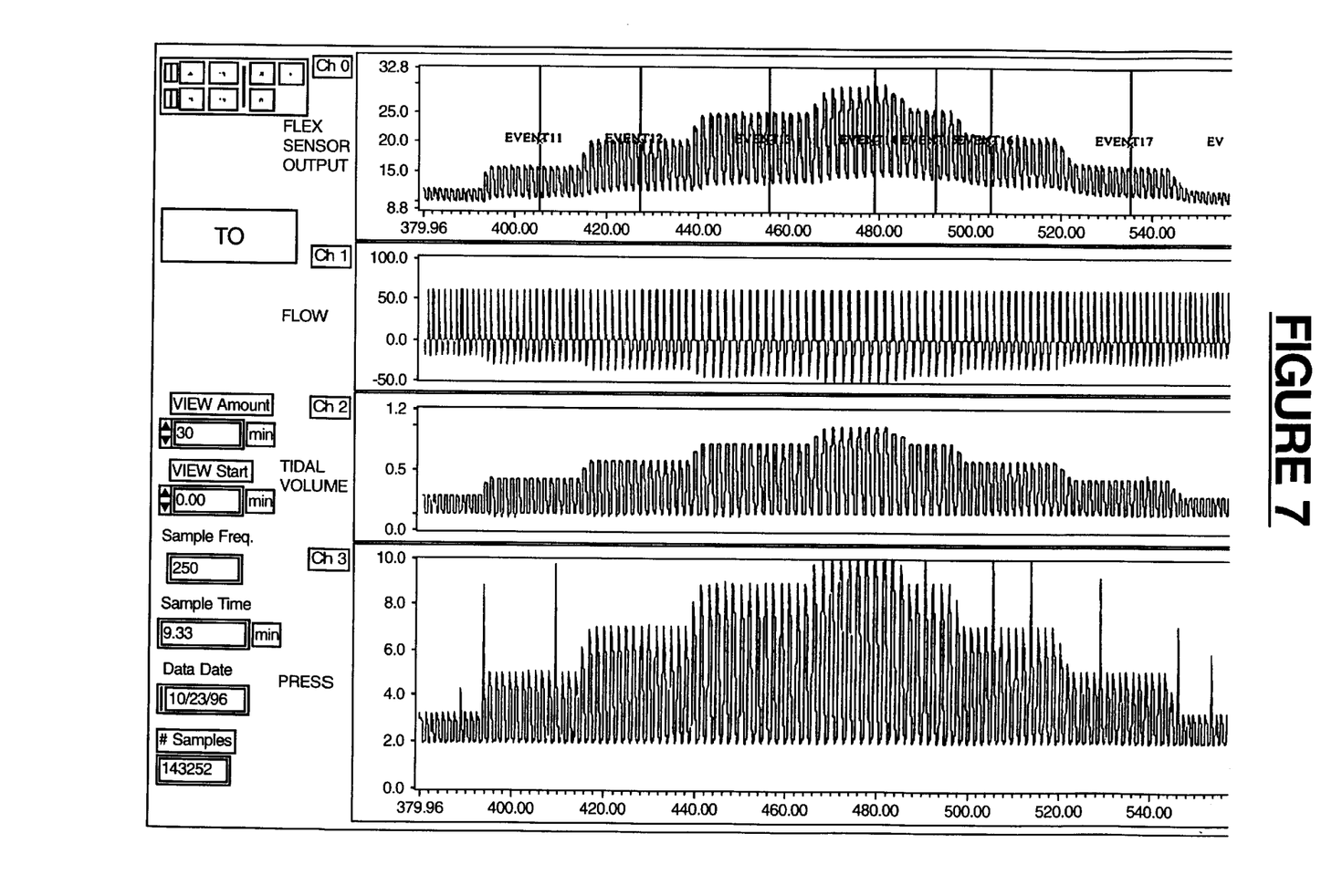
FIG. 7 is a graph showing the response of mice ventilated with a volume cycled ventilator to a device according to the invention.

A device according to the invention was tested in mice while the mice were ventilated with a volume cycled ventilator. Mice were weighed and anaesthetized with an intraperitoneal injection of a mixture of Xylazine and Ketamine (10 mg/kg and 150 mg/kg). Once an appropriate depth of anaesthesia was reached, the trachea was intubated via a tracheostomy with a blunted 18 ga. needle and ventilated with a tidal volume of about 8 ml/kg at a rate of 50 $min^{-1}$ using a volume controlled ventilator. The device of the invention (referred to in this example as the "flex sensor") was modified by covering both of its surfaces with waterproof tape to prevent changes in resistance caused by ambient humidity. The flex sensor was attached to an adjustable support and positioned to contact the chest of the mouse perpendicular to the up and down motion of the chest caused by respiration (FIG. 5). The flex sensor was connected to a circuit and the electronic signal representing the tidal volume breathing of the mouse was observed and recorded on a computer based data acquisition system (Labview). The delivered tidal volume, flow and pressure were also simultaneously recorded along with the response from the flex sensor for subsequent analysis. All data was digitized at a sampling rate of 250 $min^{-1}$. In order to test the response of the flex sensor to a wide range of volume changes, the tidal volume was increased in stepwise fashion from 0 to 10 ml in 1 ml increments using the tidal volume control of the ventilator. In order to test the ability of the flex sensor to detect slower changes in lung volume, the level of positive end expiratory pressure (PEEP) was increased in stepwise fashion from 0 to 7 cm $H_2O$ in 1 cm $H_2O$ increments. The data was subsequently recovered from the computer, analyzed and plotted. Representative sample results are shown in FIG. 6 and FIG. 7. There was a good correlation between the signal output and the tidal volume over a reasonable practical range of tidal volumes.

Figure 8:
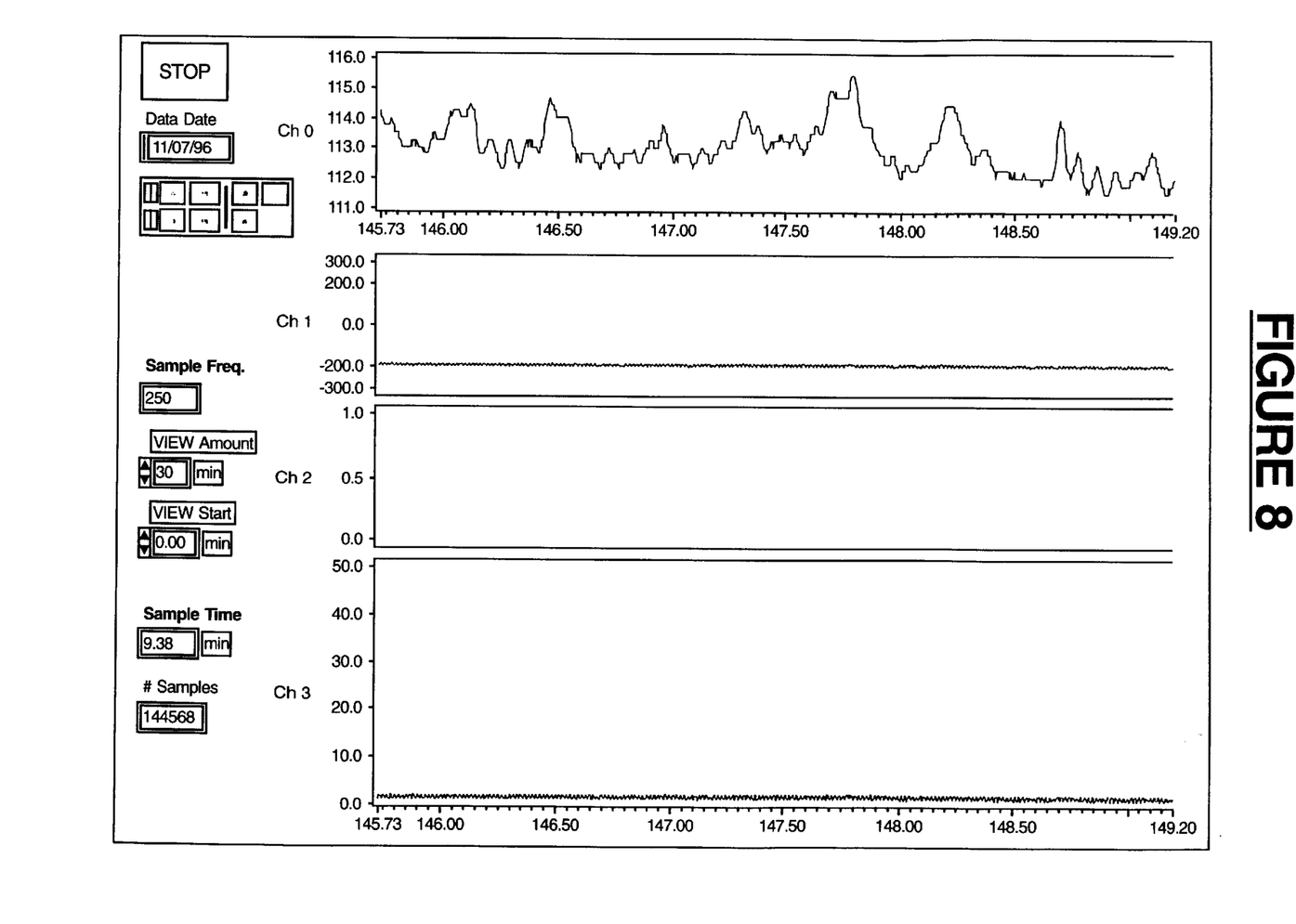
FIG. 8 is a graph showing heart rate monitored in a mouse using the device of the invention.

FIG. 8 shows monitoring of heart rate using the flex sensor. A good correlation was shown between the signal output and heart rate.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

I claim:

1. A device for monitoring tidal volume in a subject comprising a substrate for attachment to an animal or human whose tidal volume is to be monitored; sensing means attached to the substrate and connectable into an electric circuit which converts changes in tidal volume in the animal or human to a signal output, the sensing means comprising a series of semiconductive sensors and conductive sensors.

2. A device as claimed in claim 1 wherein the semiconductive sensors and conductive sensors are selected to provide an about linear relationship between signal output and tidal volume.

3. A device as claimed in claim 1 wherein the substrate is flexible.

4. A device as claimed in claim 1 wherein the substrate is elastic.

5. A device as claimed in claim 1, wherein the semiconductive sensors comprise semiconductive ink or paint deposited on selected areas of the substrate.

6. A device as claimed in claim 5 wherein the conductive sensors comprise conductive material deposited on selected areas of the semiconductive ink or paint forming alternate semiconductive/conductive and semiconductive regions.

7. A device as claimed in claim 6 wherein the conductive material is a metallic material.

8. A device as claimed in claim 6 wherein the conductive material is copper.

9. A device as claimed in claim 6 which is U-shaped, disc-shaped, or donut-shaped.

10. A device as claimed in claim 6 wherein the device is coated with a substance that facilitates the attachment of the device to a subject.

11. A device as claimed in claim 6 wherein the device is disc-shaped and the semiconductive/conductive regions and conductive regions form a ring.

12. A device as claimed in claim 6 wherein the device is disc-shaped and the semiconductive/conductive regions and conductive regions are alternate rings on the substrate.

13. A device as claimed in claim 6 wherein the device is disc-shaped and the semiconductive/conductive regions and conductive regions form an array of bands radiating from a central zone.

14. A device as claimed in claim 6 wherein the device is donut-shaped and the semiconductive/conductive regions and conductive regions form a ring.

15. A method for monitoring tidal volume in a subject comprising (a) attaching a device as claimed in claim 6 to the subject; (b) detecting signal output from the device; and (c) monitoring the tidal volume by determining the frequency or intensity of the signal output.

16. A method for monitoring tidal volume in a subject comprising (a) attaching a device as claimed in claim 9 to the subject; (b) detecting signal output from the device; and (c) monitoring the tidal volume by determining the frequency or intensity of the signal output.

17. A method for monitoring tidal volume in a subject comprising (a) attaching a device as claimed in claim 11 to the subject; (b) detecting signal output from the device; and (c) monitoring the tidal volume by determining the frequency or intensity of the signal output.

18. A method for monitoring tidal volume in a subject comprising (a) attaching a device as claimed in claim 12 to the subject; (b) detecting signal output from the device; and (c) monitoring the tidal volume by determining the frequency or intensity of the signal output.

19. A method for monitoring tidal volume in a subject comprising (a) attaching a device as claimed in claim 13 to the subject; (b) detecting signal output from the device; and (c) monitoring the tidal volume by determining the frequency or intensity of the signal output.

20. A method for monitoring tidal volume in a subject comprising (a) attaching a device as claimed in claim 14 to the subject; (b) detecting signal output from the device; and (c) monitoring the tidal volume by determining the frequency or intensity of the signal output.

* * * * *